US 10,186,664 B2

(12) United States Patent
Gessner et al.

(10) Patent No.: US 10,186,664 B2
(45) Date of Patent: Jan. 22, 2019

(54) N-FLUOROALKYL-SUBSTITUTED DIBROMONAPHTHALENE DIIMIDES AND THEIR USE AS SEMICONDUCTOR

(71) Applicant: BASF SE, Ludwigshafen (DE)

(72) Inventors: Thomas Gessner, Heidelberg (DE); Daniel Kaelblein, Mannheim (DE); Jochen Brill, Speyer (DE); Thomas Musiol, Maxdorf (DE); Frank Wuerthner, Hoechberg (DE); Sabin-Lucian Suraru, Seattle, WA (US); Matthias Stolte, Gerbrunn (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/318,566

(22) PCT Filed: Jun. 16, 2015

(86) PCT No.: PCT/IB2015/054545
§ 371 (c)(1),
(2) Date: Dec. 13, 2016

(87) PCT Pub. No.: WO2015/193808
PCT Pub. Date: Dec. 23, 2015

(65) Prior Publication Data
US 2017/0117479 A1 Apr. 27, 2017

(30) Foreign Application Priority Data
Jun. 17, 2014 (EP) .................................. 14172787

(51) Int. Cl.
H01L 51/00 (2006.01)
C07D 471/08 (2006.01)
C07D 471/06 (2006.01)
H01L 27/28 (2006.01)
C09B 57/08 (2006.01)
H01L 51/05 (2006.01)
H01L 51/42 (2006.01)

(52) U.S. Cl.
CPC ........ H01L 51/0053 (2013.01); C07D 471/06 (2013.01); C09B 57/08 (2013.01); H01L 27/28 (2013.01); H01L 51/0541 (2013.01); H01L 51/0545 (2013.01); H01L 51/0558 (2013.01); H01L 51/42 (2013.01); Y02E 10/549 (2013.01)

(58) Field of Classification Search
CPC .... C07D 471/08; H01L 51/0545; H01L 29/00
USPC ............................... 546/66; 257/40; 136/252
See application file for complete search history.

(56) References Cited

U.S. PATENT DOCUMENTS 4,461,922 A 7/1984 Gay et al.
4,539,507 A 9/1985 Vanslyke et al.
4,720,432 A 1/1988 Vanslyke et al.
4,769,292 A 9/1988 Tang et al.
6,198,091 B1 3/2001 Forrest et al.
6,198,092 B1 3/2001 Bulovic et al.
8,710,225 B2 * 4/2014 Gessner ............... C07D 471/06
257/40
2004/0046182 A1 3/2004 Chen et al.
2005/0098726 A1 5/2005 Peumans et al.
2005/0224905 A1 10/2005 Forrest et al.
2005/0227406 A1 10/2005 Shtein et al.
2006/0202195 A1 9/2006 Marks et al.
2007/0190783 A1 8/2007 Gomez et al.
(Continued)

FOREIGN PATENT DOCUMENTS

DE 10 2004 014 046 A1 9/2004
EP 0 387 715 A2 9/1990
(Continued)

OTHER PUBLICATIONS

Stolte, M. et al. Organic n-channel thin film transistors based on dichlorinated naphthalene diimides. Proceedings of SPIE, 7788, pp. 777804/1 to 777804/8, 2010.*
Subashani Maniam et al., "Unexpected Photoluminescence of Fluorinated Naphthalene Diimides", Chemistry, A European Journal, vol. 21, No. 10, XP-55416412, Jan. 29, 2015, pp. 4133-4140.
International Search Report dated Nov. 10, 2015 in PCT/IB2015/054545 filed Jun. 16, 2015.
International Preliminary Report on Patentability dated Oct. 31, 2016 in PCT/IB2015/054545 filed Jun. 16, 2015.
(Continued)

Primary Examiner — Charanjit Aulakh
(74) Attorney, Agent, or Firm — Oblon, McClelland, Maier & Neustadt, L.L.P.

(57) ABSTRACT

The present invention relates to compounds of the formula (I) where $R^1$ and $R^2$ independently of each other, are selected from 1H,1H—$C_2$-$C_{10}$-perfluoroalkyl and 1H,1H,2H,2H—$C_3$-$C_{10}$-perfluoroalkyl, except for the compound of formula (I), where $R^1$ and $R^2$ are both 1H,1H-perfluorobutyl, and to their use, especially as an n-type semiconductor.

16 Claims, No Drawings

(56) References Cited

U.S. PATENT DOCUMENTS

| | | |
|---|---|---|
| 2009/0301552 A1 | 12/2009 | Koenemann et al. |
| 2012/0059168 A1 | 3/2012 | Koenemann |
| 2013/0289279 A1* | 10/2013 | Gessner et al. ..... H01L 51/0072 546/66 |
| 2015/0123090 A1 | 5/2015 | Musiol et al. |

FOREIGN PATENT DOCUMENTS

| | | |
|---|---|---|
| EP | 0 532 798 A1 | 3/1993 |
| WO | WO 00/70655 A2 | 11/2000 |
| WO | WO 2005/019373 A2 | 3/2005 |
| WO | WO 2006/092124 A1 | 9/2006 |
| WO | WO 2007/074137 A1 | 7/2007 |
| WO | WO 2007/093643 A1 | 8/2007 |
| WO | WO 2007/116001 A2 | 10/2007 |
| WO | WO 2009/147237 A1 | 12/2009 |
| WO | WO 2010/049512 A1 | 5/2010 |
| WO | WO 2011/158211 A1 | 12/2011 |
| WO | WO 2012/095790 A1 | 7/2012 |
| WO | WO 2013/164761 A1 | 11/2013 |

OTHER PUBLICATIONS

U.S. Appl. No. 14/411,184, filed Dec. 24, 2014, U.S. Pat No. 2015/0179954, Gessner, et al.

U.S. Appl. No. 15/120,647, filed Aug. 22, 2016, Gessner, et al.

U.S. Appl. No. 15/128,455, filed Sep. 23, 2016, Unknown.

* cited by examiner

N-FLUOROALKYL-SUBSTITUTED DIBROMONAPHTHALENE DIIMIDES AND THEIR USE AS SEMICONDUCTOR

The present invention relates to N-fluoroalkyl-substituted dibromonaphthalene diimides and their use as semiconductor, in particular as semiconductor in organic electronics.

Recent developments in organic-based light-emitting diodes (OLEDs), photovoltaics (OPVs), and field-effect transistors (OFETs) have opened up many opportunities in the field of organic electronics. One of the challenges in this field is to develop thin film devices that have environmentally stable electron-transporting (n-type) organic semi-conductors with high mobility. Thus, one important key parameter of OFETs is the carrier mobility which is directly proportional to semiconductor conductivity and another key parameter is the on/off current ratio. Increasing this ratio is important for the switch-like behaviour of OFETs. The performance and stability of organic n-type materials have significantly lagged behind their p-type counterparts. Some challenges for advancing the technology of organic n-type materials include their vulnerability to ambient conditions (e.g. air) and solution-processability. For example, it is desirable for these materials to be soluble in common solvents so that they can be formulated into inks for inexpensive printing processes or can be solution-processed into thin-film form at low temperature. These technique could make OFET manufacturing simpler and more cost-effective than physical deposition techniques allow. When used in organic field-effect transistors (OFETs), the organic semiconducting materials should show a good field-effect mobility and a high on/off current ratio.

WO 2012/095790 describes 2,6-dibromo-N,N'-bis(1H,1H-perfluorobutyl)-naphthalene-[1,8:4,5]bis(dicarboximide) as intermediate compound in the preparation of thiocyanato or isothiocyanato substituted naphthalene diimide and rylene diimide compounds. The use of 2,6-dibromo-N,N'-bis(1H,1H-perfluorobutyl)-naphthalene-[1,8:4,5]bis(dicarboximide) as semiconductor in organic electronics is not described.

Naphthalene-1,8;4,5-tetracarboxylic bisimides which carry at least one substituent selected from Br, F and CN on the naphthalene scaffold, in particular those described in WO 2007/074137, have been demonstrated to be effective n-semiconductors. However, as found out by the inventors of the present invention, in some cases, the solution-processability of these compounds, the field-effect mobility and/or the on/off current ratio of these compounds in organic electronics devices are not always entirely satisfactory.

Accordingly, given potential applications in inexpensive and large-area organic electronics that can be produced by high-throughput manufacture, it is an object of the present invention to provide semiconducting compounds having desirable properties such as high field-effect mobilities, high on/off ratios, good solubility in common solvents and air stability, especially high on/off ratios, good solubility in common solvents and air stability.

These and further objects are achieved by N-fluoroalkyl substituted dibromonaphthalene diimides of formula I, defined below.

Accordingly, the present invention provides a compound of formula I

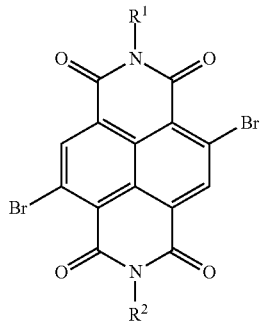

(I)

where
R¹ and R², independently of each other, are selected from 1H,1H—C$_2$-C$_{10}$-perfluoroalkyl and 1H,1H,2H,2H—C$_3$-C$_{10}$-perfluoroalkyl
except for the compound of formula I, where R¹ and R² are both 1H,1H-perfluorobutyl.

According to a further aspect of the present invention there is provided the use of a compound of formula I, as defined above and in the following, as a semiconductor material, especially for organic field effect transistors and organic photovoltaics.

The present invention also provides a thin film semiconductor comprising a compound of formula I.

According to a further aspect of the present invention there is provided an organic field-effect transistor comprising a substrate having at least one gate structure, a source electrode and a drain electrode and at least one compound of the formula I as defined above and in the following as a semiconductor material.

The compounds of formula I can be in principle used as n-type semiconductors or as p-type semiconductors. If a compound of formula I acts as n-type semiconductor or as p-type semiconductors depends inter alia on the employed gate dielectric. Gate dielectrics are usually employed in the form of a self-assembled monolayer (SAM) of suitable compounds, e.g. silanes with more or less electronegative substituents, alkyl phosphonic acid, fluoroalkyl phosphonic acid, etc. By choosing a certain SAM gate dielectric or a certain mixture of different SAM gate dielectrics, it is possible to control the properties of the semiconductor material. In electronic devices that employ a combination of two different semiconductors, e.g. organic solar cells, it depends on the corresponding semiconductor material if a compound of the formula I acts as n-type semiconductor or as p-type semiconductor. The compounds of formula I are especially suitable as n-semiconductor.

Further embodiments of the present invention are evident from the claims, the description and the examples.

In a preferred embodiment, the compound of formula I are used as a semiconductor material in organic electronics or in organic photovoltaics, especially as n-semiconductor material.

It has been found that the dibromonaphthalene diimide compounds of the present invention have semiconducting activity. Materials prepared from these compounds have demonstrated unexpected properties. It has been discovered that compounds of the present invention have high field-effect mobilities and/or good current modulation characteristics in field-effect devices (e.g., thin-film transistors). In addition, it has been discovered that compounds of the present invention can possess certain processing advantages compared to related representative compounds such as better solubility to permit solution-processability and/or good stability at ambient conditions, for example, air stability. Further, the compounds can be embedded with other components for utilization in a variety of semiconductor-based devices As used herein, the term "1H,1H—$C_2$-$C_{10}$-perfluoroalkyl" refers to a $C_1$-$C_9$-perfluoroalkyl-$CH_2$— group, which is bound to the remainder of the molecule via $CH_2$ and wherein $C_1$-$C_9$-perfluoroalkyl is a straight or branched alkyl group having 1 to 9 carbon atoms, wherein all hydrogen atoms are replaced by fluorine atoms. Examples for $C_1$-$C_9$-perfluoroalkyl are trifluoromethyl, pentafluoroethyl, n-perfluoropropyl, isoperfluoropropyl, n-perfluorobutyl, iso-perfluorobutyl, tert-perfluorobutyl, secperfluorobutyl, n-perfluoropentyl, iso-perfluoropentyl, sec-perfluoropentyl, tertperfluoropentyl, neoperfluoropentyl and the like. Examples for linear 1H,1H—$C_2$-$C_{10}$-perfluoroalkyl include 2,2,2-trifluoroethyl, 2,2,3,3,3-pentafluoropropyl, 2,2,3,3,4,4,4-heptafluorobutyl, 2,2,3,3,4,4,5,5,5-nonafluoropentyl, 2,2,3,3,4,4,5,5,6,6,6-undecafluorohexyl, 2,2,3,3,4,4,5,5,6,6,7,7,7-tridecafluoroheptyl, 2,2,3,3,4,4,5,5,6,6,7,7,8,8,8-pentadecafluorooctyl, 2,2,3,3,4,4,5,5,6,6,7,7,8,8,9,9,9-heptadecafluorononyl and 2,2,3,3,4,4,5,5,6,6,7,7,8,8,9,9,10,10,10-nonadecafluorodecyl. Examples for branched 1H,1H—$C_4$-$C_{10}$-perfluoroalkyl include 2,3,3,3-tetrafluoro-2-(trifluoromethyl)propyl, 2,3,3,4,4,4-hexafluoro-2-(trifluoromethyl)butyl, 3,3,4,4,4-pentafluoro-2,2-bis(trifluoromethyl)butyl, and the like.

As used herein, the term "1H,1H,2H,2H—$C_3$-$C_{10}$-perfluoroalkyl" refers to a $C_1$-$C_8$-perfluoroalkyl-$CH_2$—$CH_2$— group, which is bound to the remainder of the molecule via $CH_2$—$CH_2$—, and wherein $C_1$-$C_8$-perfluoroalkyl is a straight or branched alkyl group having 1 to 8 carbon atoms, wherein all hydrogen atoms are replaced by fluorine atoms as defined above. Examples for linear 1H,1H,2H,2H—$C_3$-$C_{10}$-perfluoroalkyl include 3,3,3-trifluororopropyl, 3,3,4,4,4-pentafluorobutyl, 3,3,4,4,5,5,5-heptafluoropentyl, 3,3,4,4,5,5,6,6,6-nonafluorohexyl, 3,3,4,4,5,5,6,6,7,7,7-undecafluoroheptyl, 3,3,4,4,5,5,6,6,7,7,8,8,8-tridecafluorooctyl, 3,3,4,4,5,5,6,6,7,7,8,8,9,9,9-pentadecafluorononyl and 3,3,4,4,5,5,6,6,7,7,8,8,9,9,10,10,10-heptadecafluorodecyl. Examples for branched 1H,1H—$C_5$-$C_{10}$-perfluoroalkyl include 3,4,4,4-tetrafluoro-3-(trifluoromethyl)butyl, 4,4,4-trifluoro-3,3-bis(trifluoromethyl)butyl, 3,3,5,5,5-pentafluoro-4,4-bis(trifluoromethyl)pentyl the like.

As used herein, a "n-type semiconducting material" or a "n-type semiconductor" refers to a semiconducting material having electrons as the majority current carriers. In some embodiments, when a n-type semiconducting material is deposited on a substrate, it can provide an electron mobility in excess of about $10^{-5}$ $cm^2/Vs$.

As used herein, "field effect mobility p" (also referred to as "charge transport mobility μ") refers to a measure of the velocity with which charge carriers, for example, electrons in the case of an n-type semiconducting material, move through the material under the influence of an electric field.

As used herein "the on/off current ratio" (also referred to as on/off ratio) is the ratio of the maximum drain current to the minimum drain current as a function of the gate-source voltage $V_{GS}$ in the saturation regime.

As used herein, a compound can be considered "ambient stable" or "stable at ambient conditions" when the mobility or the reduction-potential of the compound is maintained at about its initial measurement when the compound is exposed to ambient conditions, for example, air, ambient temperature, and humidity over a period of time. For example, a compound can be described as ambient stable if its mobility or reduction potential does not vary more than 20% or preferably more than 10% from its initial value after exposure to ambient conditions, i.e. air, humidity and temperature, over a period of 3 days, preferably 5 days, or more preferably 10 days or more.

As used herein, "solution-processable" refers to compounds, materials, or compositions that can be used in various solution-phase processes including spincoating, printing (e.g., inkjet printing, screen printing, pad printing, gravure printing, flexographic printing, offset printing, microcontact printing, and lithographic printing), spraying, electrospray coating, drop casting, zone-casting, dip coating, and blade coating.

With regard to the use of the compound of the formula I in an organic electronics device, the variables $R^1$, $R^2$, are, each independently, preferably selected from linear 1H,1H—$C_2$-$C_6$-perfluoroalkyl. More preferably, $R^1$ and $R^2$ are, independently of each other, selected from 2,2,2-trifluoroethyl, 2,2,3,3,3-pentafluoropropyl, 2,2,3,3,4,4,5,5,5-nonafluoropentyl and 2,2,3,3,4,4,5,5,6,6,6-undecafluorohexyl.

According to a more preferred embodiment, $R^1$ and $R^2$ have the same meaning.

In particular, the compound of formula I is selected from 2,6-dibromo-N,N'-bis(2,2,2-trifluoroethyl)-naphthalene[1,8:4,5]bis(dicarboximide);
2,6-dibromo-N,N'-bis(1H,1H-perfluoropropyl)-naphthalene[1,8:4,5]bis(dicarboximide); and
2,6-dibromo-N,N'-bis(1H,1H-perfluoropentyl)-naphthalene[1,8:4,5]bis(dicarboximide).

In a more particular embodiment, the compound of formula I is 2,6-dibromo-N,N'-bis(1H,1H-perfluoropentyl)-naphthalene[1,8:4,5]bis(dicarboximide).

The compounds of formula I can be prepared by using methods described in WO 2012/095790 and WO 2007/074137 for synthesizing analogous compounds, and the preparation is outlined by way of example in synthesis scheme 1 and also in the experimental part below. If not indicated otherwise, the variables in the synthetic scheme have the same meanings as in formula I.

Scheme 1:

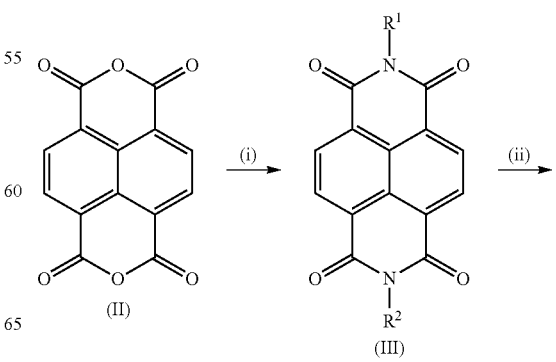

-continued

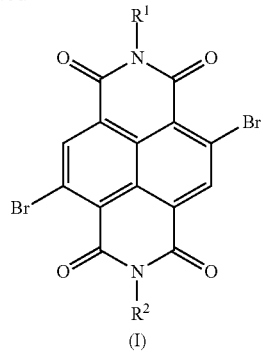

(I)

In step i) of scheme 1, the naphthalene-1,8;4,5-tetracarboxylic dianhydride of formula II is subjected to a reaction with an amine of the formula $R^1$—$NH_2$ and, if appropriate, an amine of the formula $R^2$—$NH_2$ to obtain an imide compound of the formula III.

The reaction can be carried out as described in H. E. Katz et al., Materials Research Society Symposium Proceedings (2001), 665 (Electronics, Optical and Optoelectronic Polymers and Oligomers), 271-280 or in J. H. Oh et al., Adv. Funct. Mater. 2010, 20, 2148-2156.

In step ii) of scheme 1, the imide compound of formula III is subjected to a bromination with N,N'-dibromoisocyanuric acid. The bromination in step ii) is effected using 95 to 97% strength sulfuric acid. The reaction temperature in step ii) is usually room temperature.

The compounds of formula I have at least one of the following advantages over known organic semiconductor materials:
high charge transport mobility;
air stability;
high on/off current ratio;
suitability to be employed in a solvent-based process.

In particular, the inventive compounds are notable for their air stability. They also possess high charge transport mobility. They also possess a high on/off current ratio. In addition, they are suitable to be used in a wet processing method.

The compounds of formula I are advantageously suitable for organic field-effect transistors. They may be used, for example, for the production of integrated circuits (ICs), for which customary n-channel MOSFETs (metal oxide semiconductor field-effect transistors) have been used to date. These are then CMOS-like semiconductor units, for example for microprocessors, microcontrollers, static RAM and other digital logic circuits. For the production of semiconductor materials, the compound of formula I can be processed further by one of the following processes: printing (offset, flexographic, gravure, screenprinting, inkjet, electrophotography), evaporation, laser transfer, photolithography, drop-casting. They are especially suitable for use in displays (specifically large-surface area and/or flexible displays), RFID tags, smart labels and sensors.

The compounds of formula I are advantageously suitable as electron conductors in organic field-effect transistors, organic solar cells and in organic light-emitting diodes. They are also particularly advantageous as an exciton transport material in excitonic solar cells.

The invention further provides organic field-effect transistors comprising a substrate with at least one gate structure, a source electrode and a drain electrode, and at least one compound of formula I as defined above as a semiconductor, especially n-semiconductor.

The invention further provides substrates having a plurality of organic field-effect transistors, wherein at least some of the field-effect transistors comprise at least one compound of formula I as defined above.

The invention also provides semiconductor units which comprise at least one such substrate.

A specific embodiment is a substrate with a pattern (topography) of organic field-effect transistors, each transistor comprising
an organic semiconductor disposed on the substrate;
a gate structure for controlling the conductivity of the conductive channel; and
conductive source and drain electrodes at the two ends of the channel,
the organic semiconductor consisting of at least one compound of formula I or comprising a compound of formula I. In addition, the organic field-effect transistor generally comprises a dielectric.

A specific embodiment is a substrate with a pattern (topography) of organic field-effect transistors, each transistor comprising
an organic semiconductor disposed on a buffer layer on a substrate;
a gate structure for controlling the conductivity of the conductive channel; and
conductive source and drain electrodes at the two ends of the channel,
the organic semiconductor consisting of at least one compound of formula I or comprising a compound of formula I. In addition, the organic field-effect transistor generally comprises a dielectric.

As a buffer layer, any dielectric material is suitable, for example anorganic materials such LIF, $AlO_x$, $SiO_2$ or silicium nitride or organic materials such as polyimides or polyacrylates, e.g. polymethylmethacrylate (PMMA).

A further specific embodiment is a substrate having a pattern of organic field-effect transistors, each transistor forming an integrated circuit or being part of an integrated circuit and at least some of the transistors comprising at least one compound of formula I.

Suitable substrates are in principle the materials known for this purpose. Suitable substrates comprise, for example, metals (preferably metals of groups 8, 9, 10 or 11 of the Periodic Table, such as Au, Ag, Cu), oxidic materials (such as glass, ceramics, $SiO_2$, especially quartz), semiconductors (e.g. doped Si, doped Ge), metal alloys (for example based on Au, Ag, Cu, etc.), semiconductor alloys, polymers (e.g. polyvinyl chloride, polyolefins, such as polyethylene and polypropylene, polyesters such as polyethylene terephthalate (PET), polyethylene naphthalate (PEN), polycarbonate, fluoropolymers, polyamides, polyimides, polyurethanes, polyethersulfones, polyalkyl (meth)acrylates, polystyrene and mixtures and composites thereof), inorganic solids (e.g. ammonium chloride), paper and combinations thereof. The substrates may be flexible or inflexible, and have a curved or planar geometry, depending on the desired use.

A typical substrate for semiconductor units comprises a matrix (for example a quartz or polymer matrix) and, optionally, a dielectric top layer.

Suitable dielectrics are $SiO_2$, polystyrene, poly-α-methylstyrene, polyolefins (such as polypropylene, polyethylene, polyisobutene), polyvinylcarbazole, fluorinated polymers (e.g. Cytop), cyanopullulans (e.g. CYMM), polyvinylphenol, poly-p-xylene, polyvinyl chloride, or polymers crosslinkable thermally or by atmospheric moisture. Specific dielectrics are "self-assembled nanodielectrics", i.e. polymers which are obtained from monomers comprising SiCl functionalities, for example $Cl_3SiOSiCl_3$, $Cl_3Si-(CH_2)_6-SiCl_3$, $Cl_3Si-(CH_2)_{12}-SiCl_3$, and/or which are crosslinked by atmospheric moisture or by addition of water diluted with solvents (see, for example, Facchetti, Adv. Mater. 2005, 17, 1705-1725). Instead of water, it is also possible for hydroxyl-containing polymers such as polyvinylphenol or polyvinyl alcohol or copolymers of vinylphenol and styrene to serve as crosslinking components. It is also possible for at least one further polymer to be present during the crosslinking operation, for example polystyrene, which is then also crosslinked (see Facchetti, US patent application 2006/0202195).

The substrate may additionally have electrodes, such as gate, drain and source electrodes of OFETs, which are normally localized on the substrate (for example deposited onto or embedded into a nonconductive layer on the dielectric). The substrate may additionally comprise conductive gate electrodes of the OFETs, which are typically arranged below the dielectric top layer (i.e. the gate dielectric).

In a specific embodiment, an insulator layer (gate insulating layer) is present on at least part of the substrate surface. The insulator layer comprises at least one insulator which is preferably selected from inorganic insulators, such as $SiO_2$, silicon nitride ($Si_3N_4$), etc., ferroelectric insulators, such as $Al_2O_3$, $Ta_2O_5$, $La_2O_5$, $TiO_2$, $Y_2O_3$, etc., organic insulators such as polyimides, benzocyclobutene (BCB), polyvinyl alcohols, polyacrylates, etc., and combinations thereof.

Suitable materials for source and drain electrodes are in principle electrically conductive materials. These include metals, preferably metals of groups 6, 7, 8, 9, 10 or 11 of the Periodic Table, such as Pd, Au, Ag, Cu, Al, Ni, Cr, etc. Also suitable are conductive polymers, such as PEDOT (=poly (3,4-ethylenedioxythiophene)):PSS (=poly(styrenesulfonate)), polyaniline, surface-modified gold, etc. Preferred electrically conductive materials have a specific resistance of less than $10^{-3}$ ohm×meter, preferably less than $10^{-4}$ ohm×meter, especially less than $10^{-6}$ or $10^{-7}$ ohm×meter.

In a specific embodiment, drain and source electrodes are present at least partly on the organic semiconductor material. It will be appreciated that the substrate may comprise further components as used customarily in semiconductor materials or ICs, such as insulators, resistors, capacitors, conductor tracks, etc.

The electrodes may be applied by customary processes, such as evaporation or sputtering, lithographic processes or another structuring process, such as printing techniques.

The semiconductor materials may also be processed with suitable auxiliaries (polymers, surfactants) in disperse phase by printing.

In a first preferred embodiment, the deposition of at least one compound of formula I (and if appropriate further semiconductor materials) is carried out by a gas phase deposition process (physical vapor deposition, PVD). PVD processes are performed under high-vacuum conditions and comprise the following steps: evaporation, transport, deposition. It has been found that, surprisingly, the compounds of formula I are suitable particularly advantageously for use in a PVD process, since they essentially do not decompose and/or form undesired by-products. The material deposited is obtained in high purity. In a specific embodiment, the deposited material is obtained in the form of crystals or comprises a high crystalline content. In general, for the PVD, at least one compound of formula I is heated to a temperature above its evaporation temperature and deposited on a substrate by cooling below the crystallization temperature. The temperature of the substrate in the deposition is preferably within a range from about 20 to 250° C., more preferably from 50 to 200° C. It has been found that, surprisingly, elevated substrate temperatures in the deposition of the compound of formula I can have advantageous effects on the properties of the semiconductor elements achieved.

The resulting semiconductor layers generally have a thickness which is sufficient for forming a semiconductor channel which is in contact with the source/drain electrodes. The deposition can be effected under an inert atmosphere, for example, under nitrogen, argon or helium.

The deposition is effected typically at ambient pressure or under reduced pressure. A suitable pressure range is from about $10^{-12}$ to 1.5 bar.

The compound of formula I is preferably deposited on the substrate in a thickness of from 10 to 1000 nm, more preferably from 15 to 250 nm. In a specific embodiment, the compound of the formula I is deposited at least partly in crystalline form. For this purpose, especially the above-described PVD process is suitable. Moreover, it is possible to use previously prepared organic semiconductor crystals. Suitable processes for obtaining such crystals are described by R. A. Laudise et al. in "Physical Vapor Growth of Organic Semi-Conductors", Journal of Crystal Growth 187 (1998), pages 449-454, and in "Physical Vapor Growth of Centimeter-sized Crystals of α-Hexathiophene", Journal of Crystal Growth 1982 (1997), pages 416-427, which are incorporated here by reference.

In a second preferred embodiment, the deposition of at least one compound of formula I (and if appropriate further semiconductor materials) is effected by spincoating. Surprisingly, it is thus also possible to use the compound of formula I used in accordance with the invention in a wet processing method to produce semiconductor substrates. The compound of formula I should thus also be suitable for producing semiconductor elements, especially OFETs or elements based on OFETs, by a printing process. It is possible for this purpose to use customary printing or coating processes (inkjet, flexographic, offset, gravure; intaglio printing, nanoprinting, slot die). Preferred solvents for the use of compound of formula I in a printing process are aromatic solvents, such as toluene, xylene, etc. It is also possible to add thickening substances, such as polymers, for example polystyrene, etc., to these "semiconductor inks". In this case, the dielectrics used are the aforementioned compounds.

In a preferred embodiment, the inventive field-effect transistor is a thin-film transistor (TFT). In a customary construction, a thin-film transistor has a gate electrode disposed on the substrate or buffer layer (the buffer layer being part of the substrate), a gate insulation layer disposed thereon and on the substrate, a semiconductor layer disposed on the gate insulator layer, an ohmic contact layer on the semiconductor layer, and a source electrode and a drain electrode on the ohmic contact layer.

In a preferred embodiment, the surface of the substrate, before the deposition of at least one compound of formula I (and if appropriate of at least one further semiconductor material), is subjected to a modification. This modification serves to form regions which bind the semiconductor materials and/or regions on which no semiconductor materials can be deposited. The surface of the substrate is preferably modified with at least one compound (C1) which is suitable for binding to the surface of the substrate and to the compound of formula I. In a suitable embodiment, a portion of the surface or the complete surface of the substrate is coated with at least one compound (C1) in order to enable improved deposition of at least one compound of formula I (and if appropriate further semiconductive compounds). A further embodiment comprises the deposition of a pattern of compounds of formula (C1) on the substrate by a corresponding production process. These include the mask processes known for this purpose and so-called "patterning" processes, as described, for example, in US US 20070190783, which is incorporated here fully by reference.

Suitable compound of formula (C1) are capable of a binding interaction both with the substrate and with at least one semiconductor compound of formula I. The term "binding interaction" comprises the formation of a chemical bond (covalent bond), ionic bond, coordinative interaction, van der Waals interactions, e.g. dipole-dipole interactions etc.), and combinations thereof. Suitable compounds of formula $(C_1)$ are:

silane, phosphonic acids, carboxylic acids, hydroxamic acids, such as alkyltrichlorosilanes, e.g. n-octadecyltrichlorosilane; compounds with trialkoxysilane groups, e.g. alkyltrialkoxysilanes such as n-octadecyltrimethoxysilane, n-octadecyltriethoxysilane, n-octadecyltri(n-propyl)oxysilane, n-octadecyltri(isopropyl)oxysilane; trialkoxyaminoalkylsilanes, such as triethoxyaminopropylsilane and N[(3-triethoxysilyl)propyl]ethylenediamine; trialkoxyalkyl 3-glycidyl ether silanes, such as triethoxypropyl 3-glycidyl ether silane; trialkoxyallylsilanes, such as allyltrimethoxysilane; trialkoxy(isocyanatoalkyl)silanes; trialkoxysilyl(meth)acryloyloxyalkanes and trialkoxysilyl(meth)acrylamidoalkanes, such as 1-triethoxysilyl-3-acryloyl-oxypropane.

amines, phosphines and sulfur-comprising compounds, especially thiols.

The compound (C1) is preferably selected from alkyltrialkoxysilanes, especially n-octadecyltrimethoxysilane, n-octadecyltriethoxysilane; hexaalkyldisilazanes, and especially hexamethyldisilazane (HMDS); $C_8$-$C_{30}$-alkylthiols, especially hexadecanethiol; mercaptocarboxylic acids and mercaptosulfonic acids, especially mercaptoacetic acid, 3-mercaptopropionic acid, mercaptosuccinic acid, 3-mercapto-1-propanesulfonic acid and the alkali metal and ammonium salts thereof.

Various semiconductor architectures comprising the inventive semiconductors are also conceivable, for example top contact, top gate, bottom contact, bottom gate, or else a vertical construction, for example a VOFET (vertical organic field-effect transistor), as described, for example, in US 2004/0046182.

Preferred semiconductor architectures are the following:
1. substrate, dielectric, organic semiconductor, preferably gate, dielectric, organic semiconductor, source and drain, known as "bottom-gate top-contact";
2. substrate, dielectric, organic semiconductor, preferably substrate, gate, dielectric, source and drain, organic semiconductor, known as "bottom-gate bottom-contact";
3. substrate, organic semiconductor, dielectric, preferably substrate, source and drain, organic semiconductor, dielectric, gate, known as "top-gate bottom-contact";
4. substrate, organic semiconductor, dielectric, preferably substrate, organic semiconductor, source and drain, dielectric, gate, known as "top-gate top-contact";

Preference is given to a top-gate bottom contact. Likewise, preference is given to a bottom-gate bottom-contact.

The layer thicknesses are, for example, from 10 nm to 5 µm in semiconductors, from 50 nm to 10 µm in the dielectric; the electrodes may, for example, be from 20 nm to 10 µm. The OFETs may also be combined to form other components, such as ring oscillators or inverters.

A further aspect of the invention is the provision of electronic components which comprise a plurality of semiconductor components, which may be n-type and/or p-type semiconductors. Examples of such components are field-effect transistors (FETs), bipolar junction transistors (BJTs), tunnel diodes, converters, light-emitting components, biological and chemical detectors or sensors, temperature-dependent detectors, photodetectors, such as polarization-sensitive photodetectors, gates, AND, NAND, NOT, OR, TOR and NOR gates, registers, switches, timer units, static or dynamic stores and other dynamic or sequential, logical or other digital components including programmable switches.

A specific semiconductor element is an inverter. In digital logic, the inverter is a gate which inverts an input signal. The inverter is also referred to as a NOT gate. Real inverter switches have an output current which constitutes the opposite of the input current. Typical values are, for example, (0, +5V) for TTL switches. The performance of a digital inverter reproduces the voltage transfer curve (VTC), i.e. the plot of input current against output current. Ideally, it is a staged function and, the closer the real measured curve approximates to such a stage, the better the inverter is. In a specific embodiment of the invention, the compound of formula I is used as organic semiconductors in an inverter.

The compound of formula I is also particularly advantageously suitable for use in organic photovoltaics (OPVs). Preference is given to their use in solar cells which are characterized by diffusion of excited states (exciton diffusion). In this case, one or both of the semiconductor materials utilized is notable for a diffusion of excited states (exciton mobility). Also suitable is the combination of at least one semiconductor material which is characterized by diffusion of excited states with polymers which permit conduction of the excited states along the polymer chain. In the context of the invention, such solar cells are referred to as excitonic solar cells. The direct conversion of solar energy to electrical energy in solar cells is based on the internal photo effect of a semiconductor material, i.e. the generation of electron-hole pairs by absorption of photons and the separation of the negative and positive charge carriers at a p-n transition or a Schottky contact. An exciton can form, for example, when a photon penetrates into a semiconductor and excites an electron to transfer from the valence band into the conduction band. In order to generate current, the excited state generated by the absorbed photons must, however, reach a p-n transition in order to generate a hole and an electron which then flow to the anode and cathode. The photovoltage thus generated can bring about a photocurrent in an external circuit, through which the solar cell delivers its power. The semiconductor can absorb only those photons which have an energy which is greater than its band gap. The size of the semiconductor band gap thus determines the proportion of sunlight which can be converted to electrical energy. Solar cells consist normally of two absorbing materials with different band gaps in order to very effectively utilize the solar energy. Most organic semiconductors have exciton diffusion lengths of up to 10 nm. There is still a need here for organic semiconductors through which the excited state can be passed on over very large distances. It has now been found that, surprisingly, the compounds of formula I described above are particularly advantageously suitable for use in excitonic solar cells.

Organic solar cells generally have a layer structure and generally comprise at least the following layers: anode, photoactive layer and cathode. These layers are generally applied to a substrate suitable for this purpose. The structure of organic solar cells is described, for example, in US 2005/0098726 and US 2005/0224905.

The invention provides an organic solar cell which comprises a substrate with at least one cathode and at least one anode, and at least one compound of formula I as defined above as a photoactive material. The inventive organic solar cell comprises at least one photoactive region. A photoactive region may comprise two layers, each of which has a homogeneous composition and forms a flat donor-acceptor heterojunction. A photoactive region may also comprise a mixed layer and form a donor-acceptor heterojunction in the form of a donor-acceptor bulk heterojunction. Organic solar cells with photoactive donor-acceptor transitions in the form of a bulk heterojunction are a preferred embodiment of the invention.

Suitable substrates for organic solar cells are, for example, oxidic materials, polymers and combinations thereof. Preferred oxidic materials are selected from glass, ceramic, $SiO_2$, quartz, etc. Preferred polymers are selected from polyethylene terephthalates, polyolefins (such as polyethylene and polypropylene), polyesters, fluoropolymers, polyamides, polyurethanes, polyalkyl (meth)acrylates, polystyrenes, polyvinyl chlorides and mixtures and composites.

Suitable electrodes (cathode, anode) are in principle metals, semiconductors, metal alloys, semiconductor alloys, nanowire thereof and combinations thereof. Preferred metals are those of groups 2, 8, 9, 10, 11 or 13 of the periodic table, e.g. Pt, Au, Ag, Cu, Al, In, Mg or Ca. Preferred semiconductors are, for example, doped Si, doped Ge, indium tin oxide (ITO), fluorinated tin oxide (FTO), gallium indium tin oxide (GITO), zinc indium tin oxide (ZITO), poly(3,4-ethylenedioxythiophene) poly(styrenesulfonate) (PEDOT-PSS), etc. Preferred metal alloys are, for example, alloys based on Pt, Au, Ag, Cu, etc. A specific embodiment is Mg/Ag alloys.

The material used for the electrode facing the light (the anode in a normal structure, the cathode in an inverse structure) is preferably a material at least partly transparent to the incident light. This preferably includes electrodes which have glass and/or a transparent polymer as a carrier material. Transparent polymers suitable as carriers are those mentioned above, such as polyethylene terephthalate. The electrical contact connection is generally effected by means of metal layers and/or transparent conductive oxides (TCOs). These preferably include ITO, doped ITO, FTO (fluorine doped tin oxide), AZO (aluminum doped tin oxide), ZnO, $TiO_2$, Ag, Au, Pt. Particular preference is given to ITO for contact connection. For electrical contact connection, it is also possible to use a conductive polymer, for example a poly-3,4-alkylenedioxythiophene, e.g. poly-3,4-ethyleneoxythiophene poly(styrenesulfonate) (PEDOT).

The electrode facing the light is configured such that it is sufficiently thin to bring about only minimal light absorption but thick enough to enable good charge transport of the extracted charge carriers. The thickness of the electrode layer (without carrier material) is preferably within a range from 20 to 200 nm.

In a specific embodiment, the material used for the electrode facing away from the light (the cathode in a normal structure, the anode in an inverse structure) is a material which at least partly reflects the incident light. This includes metal films, preferably of Ag, Au, Al, Ca, Mg, In, and mixtures thereof. Preferred mixtures are Mg/Al. The thickness of the electrode layer is preferably within a range from 20 to 300 nm.

The photoactive region comprises or consists of at least one layer which comprises at least one compound of formula I as defined above. In addition, the photoactive region may have one or more further layer(s). These are, for example, selected from
- layers with electron-conducting properties (electron transport layer, ETL),
- layers which comprise a hole-conducting material (hole transport layer, HTL), which need not absorb any radiation,
- exciton- and hole-blocking layers (e.g. EBLs), which must not absorb, and
- multiplication layers.

Suitable materials for these layers are described in detail hereinafter.

Suitable exciton- and hole-blocking layers are described, for example, in U.S. Pat. No. 6,451,415. Suitable materials for exciton-blocking layers are, for example, bathocuproin (BCP), 4,4',4"-tris[3-methylphenyl-N-phenylamino]triphenylamine (m-MTDATA).

The inventive solar cells comprise at least one photoactive donor-acceptor heterojunction. Optical excitation of an organic material generates excitons. In order that a photocurrent occurs, the electron-hole pair has to be separated, typically at a donor-acceptor interface between two unlike contact materials. At such an interface, the donor material forms a heterojunction with an acceptor material. When the charges are not separated, they can recombine in a process also known as "quenching", either radiatively by the emission of light of a lower energy than the incident light or nonradiatively by generation of heat. Both processes are undesired. According to the invention, at least one compound of formula I can be used as a charge generator (donor) or as electron acceptor material.

If at least one compound of formula I is used as a charge generator (donor) it can be combined with an appropriate electron acceptor material (ETM, electron transport material). Radiative excitation is followed by a rapid electron transfer to the ETM. Suitable ETMs are, for example, C60 and other fullerenes, perylene-3,4;9,10-bis(dicarboximides) (PTCDIs), or n-doped layers thereof (as described hereinafter). Preferred ETMs are C60 and other fullerenes or n-doped layers thereof.

In a first embodiment, the heterojunction has a flat configuration (see: Two layer organic photovoltaic cell, C. W. Tang, Appl. Phys. Lett., 48 (2), 183-185 (1986) or N. Karl, A. Bauer, J. Holzäpfel, J. Marktanner, M. Möbus, F. Stölzle, Mol. Cryst. Liq. Cryst., 252, 243-258 (1994).).

In a second preferred embodiment, the heterojunction is configured as a bulk (mixed) heterojunction, also referred to as an interpenetrating donor-acceptor network. Organic photovoltaic cells with a bulk heterojunction are described, for example, by C. J. Brabec, N. S. Sariciftci, J. C. Hummelen in Adv. Funct. Mater., 11 (1), 15 (2001) or by J. Xue, B. P. Rand, S. Uchida and S. R. Forrest in J. Appl. Phys. 98, 124903 (2005). Bulk heterojunctions are discussed in detail hereinafter.

The compound of formula I can be used as a photoactive material in cells with MiM, pin, pn, Mip or Min structure (M=metal, p=p-doped organic or inorganic semiconductor, n=n-doped organic or inorganic semiconductor, i=intrinsically conductive system of organic layers; see, for example, J. Drechsel et al., Org. Electron., 5 (4), 175 (2004) or Maennig et al., Appl. Phys. A 79, 1-14 (2004)).

The compound of formula I can also be used as a photoactive material in tandem cells. Suitable tandem cells are described, for example, by P. Peumans, A. Yakimov, S. R. Forrest in J. Appl. Phys., 93 (7), 3693-3723 (2003) (see also U.S. Pat. No. 4,461,922, U.S. Pat. No. 6,198,091 and U.S. Pat. No. 6,198,092) and are described in detail hereinafter. The use of compounds of formula I in tandem cells is a preferred embodiment of the invention.

The compound of formula I can also be used as a photoactive material in tandem cells which are constructed from two or more than two stacked MiM, pin, Mip or Min structures (see DE 103 13 232.5 and J. Drechsel et al., Thin Solid Films, 451452, 515-517 (2004)).

The layer thickness of the M, n, i and p layers is typically within a range from 10 to 1000 nm, more preferably from 10 to 400 nm. The layers which form the solar cell can be produced by customary processes known to those skilled in the art. These include vapor deposition under reduced pressure or in an inert gas atmosphere, laser ablation or solution or dispersion processing methods such as spincoating, knifecoating, casting methods, spray application, dipcoating or printing (e.g. inkjet, flexographic, offset, gravure; intaglio, nanoimprinting). In a specific embodiment, the entire solar cell is produced by a gas phase deposition process.

In order to improve the efficiency of organic solar cells, it is possible to shorten the mean distance through which the exciton has to diffuse in order to arrive at the next donor-acceptor interface. To this end, it is possible to use mixed layers of donor material and acceptor material which form an interpenetrating network in which internal donor-acceptor heterojunctions are possible. This bulk heterojunction is a specific form of the mixed layer, in which the excitons generated need only travel a very short distance before they arrive at a domain boundary, where they are separated.

In a preferred embodiment, the photoactive donor-acceptor transitions in the form of a bulk heterojunction are produced by a gas phase deposition process (physical vapor deposition, PVD). Suitable processes are described, for example, in US 2005/0227406, to which reference is made here. To this end, a compound of formula I and a complementary semiconductor material can be subjected to a gas phase deposition in the manner of a cosublimation. PVD processes are performed under high-vacuum conditions and comprise the following steps: evaporation, transport, deposition. The deposition is effected preferably at a pressure within a range from about $10^{-2}$ mbar to $10^{-8}$ mbar, for example from $10^{-5}$ to $10^{-8}$ mbar. The deposition rate is preferably within a range from 0.01 to 100 nm/s. The deposition can be effected in an inert gas atmosphere, for example under nitrogen, helium or argon. The temperature of the substrate during the deposition is preferably within a range from −100 to 300° C., more preferably from −50 to 250° C.

The other layers of the organic solar cell can be produced by known processes. These include vapor deposition under reduced pressure or in an inert gas atmosphere, laser ablation, or solution or dispersion processing methods such as spincoating, knifecoating, casting methods, spray application, dipcoating or printing (e.g. inkjet, flexographic, offset, gravure; intaglio, nanoimprinting). In a specific embodiment, the entire solar cell is produced by a gas phase deposition process.

The photoactive layer (homogeneous layer or mixed layer) can be subjected to a thermal treatment directly after production thereof or after production of further layers which form the solar cell. Such a heat treatment can in many cases further improve the morphology of the photoactive layer. The temperature is preferably within a range from about 60° C. to 300° C. The treatment time is preferably within a range from 1 minute to 3 hours. In addition or alternatively to a thermal treatment, the photoactive layer (mixed layer) can be subjected to a treatment with a solvent-containing gas directly after production thereof or after production of further layers which form the solar cell. In a suitable embodiment, saturated solvent vapors in air are used at ambient temperature. Suitable solvents are toluene, xylene, chloroform, N-methylpyrrolidone, dimethylformamide, ethyl acetate, chlorobenzene, dichloromethane and mixtures thereof. The treatment time is preferably within a range from 1 minute to 3 hours.

In a suitable embodiment, the inventive solar cells are present as an individual cell with flat heterojunction and normal structure. In a specific embodiment, the cell has the following structure:

an at least partly transparent conductive layer (top electrode, anode) (11)
a hole-conducting layer (hole transport layer, HTL) (12)
a layer which comprises a donor material (13)
a layer which comprises an acceptor material (14)
an exciton-blocking and/or electron-conducting layer (15)
a second conductive layer (back electrode, cathode) (16)

The donor material preferably comprises at least one compound of the formula I or consists of a compound of the formula I. The acceptor material preferably comprises at least one fullerene or fullerene derivative, or consists of a fullerene or fullerene derivative. The acceptor material preferably comprises C60 or PCBM ([6,6]-phenyl-C61-butyric acid methyl ester).

The essentially transparent conductive layer (11) (anode) comprises a carrier, such as glass or a polymer (e.g. polyethylene terephthalate) and a conductive material, as described above. Examples include ITO, doped ITO, FTO, ZnO, AZO, etc. The anode material can be subjected to a surface treatment, for example with UV light, ozone, oxygen plasma, $Br_2$, etc. The layer (11) should be sufficiently thin to enable maximum light absorption, but also sufficiently thick to ensure good charge transport. The layer thickness of the transparent conductive layer (11) is preferably within a range from 20 to 200 nm.

Solar cells with normal structure optionally have a hole-conducting layer (HTL). This layer comprises at least one hole-conducting material (hole transport material, HTM). Layer (12) may be an individual layer of essentially homogeneous composition or may comprise two or more than two sublayers.

Hole-conducting materials (HTM) suitable for forming layers with hole-conducting properties (HTL) preferably comprise at least one material with high ionization energy. The ionization energy is preferably at least 5.0 eV, more preferably at least 5.5 eV. The materials may be organic or inorganic materials. Organic materials suitable for use in a layer with hole-conducting properties are preferably selected from poly(3,4-ethylenedioxythiophene) poly(styrenesulfonate) (PEDOT-PSS), Ir-DPBIC (tris-N,N'-diphenyl-benzimidazol-2-ylideneiridium(III)), N,N'-diphenyl-N,N'-bis(3-methylphenyl)-1,1'-diphenyl-4,4'-diamine (α-NPD), 2,2',7,7'-tetrakis(N,N-di-p-methoxyphenylamine)-9,9'-spirobifluorene (spiro-MeOTAD), etc. and mixtures thereof. The organic materials may, if desired, be doped with a p-dopant which has a LUMO within the same range as or lower than the HOMO of the hole-conducting material. Suitable dopants are, for example, 2,3,5,6-tetrafluoro-7,7,8,8-tetracyanoquinodimethane ($F_4TCNQ$), $WO_3$, $MoO_3$, etc.

Inorganic materials suitable for use in a layer with hole-conducting properties are preferably selected from $WO_3$, $MoO_3$, etc.

If present, the thickness of the layers with hole-conducting properties is preferably within a range from 5 to 200 nm, more preferably 10 to 100 nm.

Layer (13) comprises at least one compound of formula I. The thickness of the layer should be sufficient to absorb a maximum amount of light, but thin enough to enable effective dissipation of the charge. The thickness of the layer (13) is preferably within a range from 5 nm to 1 µm, more preferably from 5 to 100 nm.

Layer (14) comprises at least one acceptor material. The acceptor material preferably comprises at least one fullerene or fullerene derivative. Alternatively or additionally suitable acceptor materials are specified hereinafter. The thickness of the layer should be sufficient to absorb a maximum amount of light, but thin enough to enable effective dissipation of the charge. The thickness of the layer (14) is preferably within a range from 5 nm to 1 µm, more preferably from 5 to 80 nm.

Solar cells with normal structure optionally comprise an exciton-blocking and/or electron-conducting layer (15) (EBL/ETL). Suitable materials for exciton-blocking layers generally have a greater band gap than the materials of layer (13) and/or (14). They are firstly capable of reflecting excitons and secondly enable good electron transport through the layer. The materials for the layer (15) may comprise organic or inorganic materials. Suitable organic materials are preferably selected from 2,9-dimethyl-4,7-diphenyl-1,10-phenanthroline (BCP), 4,7-diphenyl-1,10-phenanthroline (Bphen), 1,3-bis[2-(2,2'-bipyridin-6-yl)-1,3,4-oxadiazo-5-yl]benzene (BPY-OXD), etc. The organic materials may, if desired, be doped with an n-dopant which has a HOMO within the same range as or lower than the LUMO of the electron-conducting material. Suitable dopants are, for example, $Cs_2CO_3$, Pyronin B (PyB), Rhodamine B, cobaltocenes, etc. Inorganic materials suitable for use in a layer with electron-conducting properties are preferably selected from ZnO, etc. If present, the thickness of the layer (15) is preferably within a range from 5 to 500 nm, more preferably 10 to 100 nm.

Layer 16 is the cathode and preferably comprises at least one compound with low work function, more preferably a metal such as Ag, Al, Mg, Ca, etc. The thickness of the layer (16) is preferably within a range from about 10 nm to 10 µm, e.g. 10 nm to 60 nm.

In a further suitable embodiment, the inventive solar cells are present as an individual cell with a flat heterojunction and inverse structure.

In a specific embodiment, the cell has the following structure:

an at least partly transparent conductive layer (cathode) (11)
an exciton-blocking and/or electron-conducting layer (12)
a layer which comprises an acceptor material (13)
a layer which comprises a donor material (14)
a hole-conducting layer (hole transport layer, HTL) (15)
a second conductive layer (back electrode, anode) (16)

With regard to suitable and preferred materials for the layers (11) to (16), reference is made to the above remarks regarding the corresponding layers in solar cells with normal structure.

In a further preferred embodiment, the inventive solar cells are present as an individual cell with normal structure and have a bulk heterojunction. In a specific embodiment, the cell has the following structure:

an at least partly transparent conductive layer (anode) (21)
a hole-conducting layer (hole transport layer, HTL) (22)
a mixed layer which comprises a donor material and an acceptor material, which form a donor-acceptor heterojunction in the form of a bulk heterojunction (23)
an electron-conducting layer (24)
an exciton-blocking and/or electron-conducting layer (25)
a second conductive layer (back electrode, cathode) (26)

The layer (23) comprises at least one compound of formula I as a photoactive material, e.g. as a donor material. The layer (23) additionally comprises a complementary semiconductor material, e.g. at least one fullerene or fullerene derivative as an acceptor material. The layer (23) comprises especially C60 or PCBM ([6,6]-phenyl-C61-butyric acid methyl ester) as an acceptor material.

With regard to layer (21), reference is made completely to the above remarks regarding layer (11).

With regard to layer (22), reference is made completely to the above remarks regarding layer (12).

Layer (23) is a mixed layer which comprises at least one compound of formula I as a semiconductor material. In addition, layer (23) comprises at least one complementary semiconductor material. As described above, the layer (23) can be produced by coevaporation or by solution processing using customary solvents. The mixed layer comprises preferably 10 to 90% by weight, more preferably 20 to 80% by weight, of at least one compound of formula I, based on the total weight of the mixed layer. The mixed layer comprises preferably 10 to 90% by weight, more preferably 20 to 80% by weight, of at least one acceptor material, based on the total weight of the mixed layer. The thickness of the layer (23) should be sufficient to absorb a maximum amount of light, but thin enough to enable effective dissipation of the charge. The thickness of the layer (23) is preferably within a range from 5 nm to 1 µm, more preferably from 5 to 200 nm, especially 5 to 80 nm.

Solar cells with a bulk heterojunction comprise an electron-conducting layer (24) (ETL). This layer comprises at least one electron transport material (ETM). Layer (24) may be a single layer of essentially homogeneous composition or may comprise two or more than two sublayers. Suitable materials for electron-conducting layers generally have a low work function or ionization energy. The ionization energy is preferably not more than 3.5 eV. Suitable organic materials are preferably selected from the aforementioned fullerenes and fullerene derivatives, 2,9-dimethyl-4,7-diphenyl-1,10-phenanthroline (BCP), 4,7-diphenyl-1,10-phenanthroline (Bphen), 1,3-bis[2-(2,2'-bipyridin-6-yl)-1,3,4-oxadiazo-5-yl]benzene (BPY-OXD), etc. The organic materials used in layer (24) may, if desired, be doped with an n-dopant which has a HOMO within the same range as or lower than the LUMO of the electron-conducting material. Suitable dopants are, for example, $Cs_2CO_3$, Pyronin B (PyB), Rhodamine B, cobaltocenes, etc. The thickness of the layer (23) is, if present, preferably within a range from 1 nm to 1 µm, particularly 5 to 60 nm.

With regard to layer (25), reference is made completely to the above remarks regarding layer (15).

With regard to layer (26), reference is made completely to the above remarks regarding layer (16).

Solar cells with a donor-acceptor heterojunction in the form of a bulk heterojunction can be produced by a gas phase deposition process as described above. With regard to deposition rates, substrate temperature during the deposition and thermal aftertreatment, reference is made to the above remarks.

In a further preferred embodiment, the inventive solar cells are present as an individual cell with inverse structure and have a bulk heterojunction.

In a particularly preferred embodiment, the inventive solar cell is a tandem cell.

A tandem cell consists of two or more than two (e.g. 3, 4, 5, etc.) subcells. A single subcell, some of the subcells or all subcells may have photoactive donor-acceptor heterojunctions. Each donor-acceptor heterojunction may be in the form of a flat heterojunction or in the form of a bulk heterojunction. Preferably, at least one of the donor-acceptor heterojunctions is in the form of a bulk heterojunction. According to the invention, the photoactive layer of at least one subcell comprises a compound of formula I. Preferably, the photoactive layer of at least one subcell comprises a compound of formula I and at least one fullerene or fullerene derivative. More preferably, the semiconductor mixture used in the photoactive layer of at least one subcell consists of a compound of formula I and $C_{60}$ or [6,6]-phenyl-C61-butyric acid methyl ester.

The subcells which form the tandem cell may be connected in parallel or in series. The subcells which form the tandem cell are preferably connected in series. There is preferably an additional recombination layer in each case between the individual subcells. The individual subcells have the same polarity, i.e. generally either only cells with normal structure or only cells with inverse structure are combined with one another.

The inventive tandem cell preferably comprises a transparent conductive layer (layer 31). Suitable materials are those specified above for the individual cells. Layers 32 and 34 constitute subcells. "Subcell" refers here to a cell as defined above without cathode and anode. The subcells may, for example, either all have a compound of formula I used in accordance with the invention in the photoactive layer (preferably in combination with a fullerene or fullerene derivative, especially C60) or have other combinations of semiconductor materials, for example C60 with zinc phthalocyanine, C60 with oligothiophene (such as DCV5T). In addition, individual subcells may also be configured as dye-sensitized solar cells or polymer cells.

In all cases, preference is given to a combination of materials which exploit different regions of the spectrum of the incident light, for example of natural sunlight. For instance, the combination of a compound of formula I and fullerene or fullerene derivative used in accordance with the invention absorbs in the long-wave region of sunlight. Cells based on at least one perylene compound as described, for example, in International patent application WO2011158211, absorb primarily in the short-wave range. Thus, a tandem cell composed of a combination of these subcells should absorb radiation in the range from about 400 nm to 900 nm. Suitable combination of subcells should thus allow the spectral range utilized to be extended. For optimal performance properties, optical interference should be considered. For instance, subcells which absorb at relatively short wavelengths should be arranged closer to the metal top contact than subcells with longer-wave absorption.

With regard to layer (31), reference is made completely to the above remarks regarding layers (11) and (21).

With regard to layers (32) and (34), reference is made completely to the above remarks regarding layers (12) to (15) for flat heterojunctions and (22) to (25) for bulk heterojunctions.

Layer 33 is a recombination layer. Recombination layers enable the charge carriers from one subcell to recombine with those of an adjacent subcell. Small metal clusters are suitable, such as Ag, Au or combinations of highly n- and p-doped layers. In the case of metal clusters, the layer thickness is preferably within a range from 0.5 to 5 nm. In the case of highly n- and p-doped layers, the layer thickness is preferably within a range from 5 to 40 nm. The recombination layer generally connects the electron-conducting layer of a subcell to the hole-conducting layer of an adjacent subcell. In this way, further cells can be combined to form the tandem cell.

Layer 36 is the top electrode. The material depends on the polarity of the subcells. For subcells with normal structure, preference is given to using metals with a low work function, such as Ag, Al, Mg, Ca, etc. For subcells with inverse structure, preference is given to using metals with a high work function, such as Au or Pt, or PEDOT-PSS.

In the case of subcells connected in series, the overall voltage corresponds to the sum of the individual voltages of all subcells. The overall current, in contrast, is limited by the lowest current of one subcell. For this reason, the thickness of each subcell should be optimized such that all subcells have essentially the same current.

Examples of different kinds of donor-acceptor heterojunctions are a donor-acceptor double layer with a flat heterojunction, or the heterojunction is configured as a hybrid planar-mixed heterojunction or gradient bulk heterojunction or annealed bulk heterojunction.

The production of a hybrid planar-mixed heterojunction is described in Adv. Mater. 17, 66-70 (2005). In this structure, mixed heterojunction layers which were formed by simultaneous evaporation of acceptor and donor material are present between homogeneous donor and acceptor material.

In a specific embodiment of the present invention, the donor-acceptor-heterojunction is in the form of a gradient bulk heterojunction. In the mixed layers composed of donor and acceptor materials, the donor-acceptor ratio changes gradually. The form of the gradient may be stepwise or linear. In the case of a stepwise gradient, the layer 01 consists, for example, of 100% donor material, layer 02 has a donor/acceptor ratio>1, layer 03 has a donor/acceptor ratio=1, layer 04 has a donor/acceptor ratio<1, and layer 05 consists of 100% acceptor material. In the case of a linear gradient, layer 01 consists, for example, of 100% donor material, layer 02 has a decreasing ratio of donor/acceptor, i.e. the proportion of donor material decreases in a linear manner in the direction of layer 03, and layer 03 consists of 100% acceptor material. The different donor-acceptor ratios can be controlled by means of the deposition rate of each and every material. Such structures can promote the percolation path for charges.

In a further specific embodiment of the present invention, the donor-acceptor heterojunction is configured as an annealed bulk heterojunction; see, for example, Nature 425, 158-162, 2003. The process for producing such a solar cell comprises an annealing step before or after the metal deposition. As a result of the annealing, donor and acceptor materials can separate, which leads to more extended percolation paths.

In a further specific embodiment of the present invention, the organic solar cells are produced by organic vapor phase deposition, either with a flat or a controlled heterojunction architecture. Solar cells of this type are described in Materials, 4, 2005, 37.

The organic solar cells of the invention preferably comprise at least one photoactive region which comprises at least one compound of the formula I, which is in contact with at least one complementary semiconductor. In addition to compound of formula I, the semiconductor materials listed hereinafter are suitable in principle for use in solar cells according to the invention.

Preferred further semiconductors are fullerenes and fullerene derivatives, preferably selected from $C_{60}$, $C_{70}$, $C_{84}$, phenyl-$C_{61}$-butyric acid methyl ester ([60]PCBM), phenyl-$C_{71}$-butyric acid methyl ester ([71]PCBM), phenyl-$C_{84}$-butyric acid methyl ester ([84]PCBM), phenyl-$C_{61}$-butyric acid butyl ester ([60]PCBB), phenyl-$C_{61}$-butyric acid octyl ester ([60]PCBO), thienyl-$C_{61}$-butyric acid methyl ester ([60]ThCBM) and mixtures thereof. Particular preference is given to $C_{60}$, [60]PCBM and mixtures thereof. Preference is given to those fullerenes which are vaporizable, for example C60 or C70.

Fullerenes and fullerene derivatives in combination with at least one compound of the formula I usually act as acceptors.

Suitable further semiconductors are perylene diimides different from the compounds of formula I. Suitable are e.g. perylene diimides of the formula

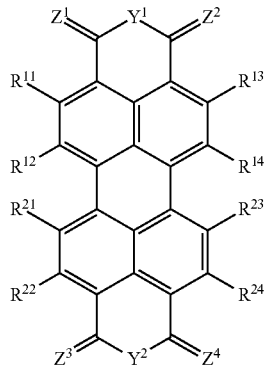

in which
the $R^{11}$, $R^{12}$, $R^{13}$, $R^{14}$, $R^{21}R^{22}$, $R^{23}$ and $R^{24}$ radicals are each independently hydrogen, halogen or groups other than halogen, $Y^1$ is O or $NR^a$ where $R^a$ is hydrogen or an organyl radical, $Y^2$ is O or $NR^b$ where $R^b$ is hydrogen or an organyl radical, $Z^1$, $Z^2$, $Z^3$ and $Z^4$ are each O, where, in the case that $Y^1$ is $NR^a$, one of the $Z^1$ and $Z^2$ radicals may also be $NR^c$, where the $R^a$ and $R^c$ radicals together are a bridging group having 2 to 5 atoms between the flanking bonds, and where, in the case that $Y^2$ is $NR^b$, one of the $Z^3$ and $Z^4$ radicals may also be $NR^d$, where the $R^b$ and $R^d$ radicals together are a bridging group having 2 to 5 atoms between the flanking bonds.

Suitable perylene diimides are, for example, described in WO 2007/074137, WO 2007/093643 and WO 2007/116001, to which reference is made here.

Perylene diimides in combination with at least one compound of the formula I may act as donors or acceptors, depending inter alia on the substituents of the perylene diimides.

Further suitable semiconductors are thiophene compounds. These are preferably selected from thiophenes, oligothiophenes and substituted derivatives thereof. Suitable oligothiophenes are quaterthiophenes, quinquethiophenes, sexithiophenes, α,ω-di($C_1$-$C_8$)-alkyloligothiophenes, such as α,ω-dihexylquaterthiophenes, α,ω-dihexylquinquethiophenes and α,ω-dihexylsexithiophenes, poly(alkylthiophenes) such as poly(3-hexylthiophene), bis(dithienothiophenes), anthradithiophenes and dialkylanthradithiophenes such as dihexylanthradithiophene, phenylene-thiophene (P-T) oligomers and derivatives thereof, especially α,ω-alkyl-substituted phenylene-thiophene oligomers.

Further thiophene compounds suitable as semiconductors are preferably selected from compounds like
α,α'-bis(2,2-dicyanovinyl)quinquethiophene (DCV5T),
(3-(4-octylphenyl)-2,2'-bithiophene) (PTOPT),
and acceptor-substituted oligothiophenes as described in WO 2006/092124.

Thiophene compounds in combination with at least one compound of the formula I usually act as donors.

Further semiconductors suitable as donors are merocyanines as described in WO 2010/049512.

All aforementioned semiconductors may be doped. The conductivity of semiconductors can be increased by chemical doping techniques using dopants. An organic semiconductor material may be doped with an n-dopant which has a HOMO energy level which is close to or higher than the LUMO energy level of the electron-conducting material. An organic semiconductor material may also be doped with a p-dopant which has a LUMO energy level which is close to or higher than the HOMO energy level of the hole-conducting material. In other words, in the case of n-doping an electron is released from the dopant, which acts as the donor, whereas in the case of p-doping the dopant acts as an acceptor which accepts an electron.

Suitable dopants for the compounds I according to the invention and for p-semiconductors in general are, for example, selected from $WO_3$, $MoO_3$, 2,3,5,6-tetrafluoro-7,7,8,8-tetracyanoquinodimethane ($F_4$-TCNQ), 3,6-difluoro-2,5,7,7,8,8-hexacyanoquinodimethane, dichlorodicyanoquinone (DDQ) or tetracyanoquinodimethane (TCNQ). A preferred dopant is 3,6-difluoro-2,5,7,7,8,8-hexacyanoquinodimethane.

Further suitable dopants are, for example, selected from $Cs_2CO_3$, LiF, Pyronin B (PyB), rhodamine derivatives, cobaltocenes, etc. Preferred dopants are Pyronin B and rhodamine derivatives, especially rhodamine B.

The dopants are typically used in an amount of up to 10 mol %, preferably up to 5 mol %, based on the amount of the semiconductor to be doped.

The invention further provides an electroluminescent (EL) arrangement comprising an upper electrode, a lower electrode, wherein at least one of said electrodes is transparent, an electroluminescent layer and optionally an auxiliary layer, wherein the electroluminescent arrangement comprises at least one compound of the formula I as defined above. An EL arrangement is characterized by the fact that it emits light when an electrical voltage is applied with flow of current. Such arrangements have been known for a long time in industry and technology as light-emitting diodes (LEDs). Light is emitted on account of the fact that positive charges (holes) and negative charges (electrons) combine with the emission of light. In the sense of this application the terms electroluminescing arrangement and organic light-emitting diode (OLEDs) are used synonymously. As a rule, EL arrangements are constructed from several layers. At least on of those layers contains one or more organic charge transport compounds. The layer structure is in principle as follows:
1. Carrier, substrate
2. Base electrode (anode)
3. Hole-injecting layer
4. Hole-transporting layer 5. Light-emitting layer
6. Electron-transporting layer
7. Electron-injecting layer
8. Top electrode (cathode)
9. Contacts
10. Covering, encapsulation.

This structure represents the most general case and can be simplified by omitting individual layers, so that one layer performs several tasks. In the simplest case an EL arrangement consists of two electrodes between which an organic layer is arranged, which fulfils all functions, including emission of light. The structure of organic light-emitting diodes and processes for their production are known in principle to those skilled in the art, for example from WO 2005/019373. Suitable materials for the individual layers of OLEDs are disclosed, for example, in WO 00/70655. Reference is made here to the disclosure of these documents. In principle OLEDs according to the invention can be produced by methods known to those skilled in the art. In a first embodiment, an OLED is produced by successive vapor deposition of the individual layers onto a suitable substrate. For vapor deposition, it is possible to use customary techniques such as thermal evaporation, chemical vapor deposition and others. In an alternative embodiment, the organic layers may be coated from solutions or dispersions in suitable solvents, for which coating techniques known to those skilled in the art are employed.

Suitable as substrate 1 are transparent carriers, such as glass or plastics films (for example polyesters, such as polyethylene terephthalate or polyethylene naphthalate, polycarbonate, polyacrylate, polysulphone, polyimide foil). Suitable as transparent and conducting materials are a) metal oxide, for example indium-tin oxide (ITO), tin oxide (NESA), etc. and b) semi-transparent metal films, for example Au, Pt, Ag, Cu, etc.

The compound of formula I preferably serve as a charge transport material (electron conductor). Thus, at least one compound of the formula I as defined above is preferably used in a hole-injecting layer, hole transporting layer or as part of a transparent electrode.

In the EL applications according to the invention low molecular weight or oligomeric as well as polymeric materials may be used as light-emitting layer 5. The substances are characterized by the fact that they are photoluminescing. Accordingly, suitable substances are for example fluorescent dyes and fluorescent products that are forming oligomers or are incorporated into polymers. Examples of such materials are coumarins, perylenes, anthracenes, phenanthrenes, stilbenes, distyryls, methines or metal complexes such as $Alq_3$ (tris(8-hydroxyquinolinato)aluminium), etc. Suitable polymers include optionally substituted phenylenes, phenylene vinylenes or polymers with fluorescing segments in the polymer side chain or in the polymer backbone. A detailed list is given in EP-A-532 798. Preferably, in order to increase the luminance, electron-injecting or hole-injecting layers (3 and/or 7) can be incorporated into the EL arrangements. A large number of organic compounds that transport charges (holes and/or electrons) are described in the literature. Mainly low molecular weight substances are used, which are for example vacuum evaporated in a high vacuum. A comprehensive survey of the classes of substances and their use is given for example in the following publications: EP-A 387 715, U.S. Pat. No. 4,539,507, U.S. Pat. No. 4,720,432 and U.S. Pat. No. 4,769,292. A preferred material is PEDOT (poly-(3,4-ethylenedioxythiophene)) which can also be employed in the transparent electrode of the OLEDs.

As a result of the inventive use of the compounds I, it is possible to obtain OLEDs with high efficiency. The inventive OLEDs can be used in all devices in which electroluminescence is useful. Suitable devices are preferably selected from stationary and mobile visual display units. Stationary visual display units are, for example, visual display units of computers, televisions, visual display units in printers, kitchen appliances and advertising panels, illuminations and information panels. Mobile visual display units are, for example, visual display units in cell phones, laptops, digital cameras, vehicles and destination displays on buses and trains. Moreover, the compounds I may be used in OLEDs with inverse structure. The compounds I in these inverse OLEDs are in turn preferably used in the light-emitting layer. The structure of inverse OLEDs and the materials typically used therein are known to those skilled in the art.

Before they are used as charge transport materials or exciton transport materials, it may be advisable to subject the compound of formula I to a purification process. The invention is illustrated in detail with reference to the non-restrictive examples which follow.

EXAMPLES

Example 1 (Comparison, Compound (21) of WO 2007/074137)

2,6-Dibromo-N,N'-bis(1H,1H-perfluorobutyl)-naphthalene[1,8:4,5]bis(dicarboximide) (compound of the formula I, where $R^1$ and $R^2$ are 2,2,3,3,3,4,4,4-heptafluorobutyl)

1.17 g (3.96 mmol) of 97% strength N,N'-dibromoisocyanuric acid were added to a solution of 2.00 g (3.17 mmol) of N,N'-bis(1H,1H-perfluorobutyl)-naphthalene[1,8:4,5]bis(dicarboximide) [described in H. E. Katz et al., Materials Research Society Symposium Proceedings (2001), 665 (Electronics, Optical and Optoelectronic Polymers and Oligomers), 271-280] in 240 mL of 95 to 97% strength sulfuric acid at room temperature. The reaction flask was darkened with aluminium foil. The solution was stirred for 28 hours at room temperature. Subsequently, the solution was poured on 1.5 kg of ice and neutralized with NaOH. The aqueous phase was extracted twice with 750 mL of dichloromethane. The combined organic extracts were dried over magnesium sulfate, filtered and concentrated to dryness. The residue was suspended in n-heptane and filtered. The filter cake obtained was dried to yield 2.29 g of a yellow solid. Recrystallization from 80 mL of isobutanol yielded 2.06 g (83% yield) of a yellow solid showing only one spot in thin-layer chromatography. A sample was sublimed at 175° C. ($1.2 \times 10^{-6}$ mbar). The melting point of the sublimed sample was 323° C.

$^1$H-NMR (400 MHz, $D_8$-THF): δ=9.00 (s, 2H), 5.08 (t, 4H) ppm.

Example 2

2,6-Dibromo-N,N'-bis(2,2,2-trifluoroethyl)-naphthalene[1,8:4,5]bis(dicarboximide) (compound of formula I, where $R^1$ and $R^2$ are 2,2,2-trifluoroethyl)

2.1 N,N'-Bis(2,2,2-trifluoroethyl)-naphthalene[1,8:4,5]bis(dicarboximide)

The title compound was prepared as described in H. E. Katz et al., Materials Research Society Symposium Proceedings (2002), 665 (Electronics, Optical and Optoelectronic Polymers and Oligomers), 271-280.

$^1$H-NMR (400 MHz, CDCl$_3$): δ=8.86 (s, 4H), 4.96 (q, $J_{HF}$=8.44 Hz, 4H) ppm

2.2 2,6-Dibromo-N,N'-bis(2,2,2-trifluoroethyl)-naphthalene[1,8:4,5]bis(dicarboximide)

0.587 g (2.05 mmol) of N,N'-dibromoisocyanuric acid were added to a solution of 0.80 g (1.9 mmol) of N,N'-bis(2,2,2-trifluoroethyl)-naphthalene-[1,8:4,5]bis(dicarboximide) in 160 mL of 95 to 97% strength sulfuric acid at room temperature. The solution was stirred for 40 hours at room temperature. Subsequently, the reaction mixture was poured on 1 L of icewater. The precipitate was filtered off and purified by column chromatography (dichloromethane/pentane 1:1) several times, and then by recrystallization in o-xylene. 0.060 g (5% yield) of a light yellow solid were obtained.

$^1$H-NMR (400 MHz, CDCl$_3$): δ=9.08 (s, 2H), 4.97 (q, 4H, J=8.56 Hz) ppm.

Example 3

2,6-Dibromo-N,N'-bis(1H,1H-perfluoropropyl)-naphthalene[1,8:4,5]bis(dicarboximide) (compound of the formula I, where R$^1$ and R$^2$ are 2,2,3,3,3-pentafluoropropyl)

3.1 N,N'-Bis(1H,1H-perfluoropropyl)-naphthalene[1,8:4,5]bis(dicarboximide)

The title compound was prepared as described in H. E. Katz et al., Materials Research Society Symposium Proceedings (2002), 665 (Electronics, Optical and Optoelectronic Polymers and Oligomers), 271-280.

$^1$H-NMR (400 MHz, CDCl$_3$): δ=8.87 (s, 4H), 4.99 (q, $J_{HF}$=14.4 Hz, 4H) ppm

3.2 2,6-Dibromo-N,N'-bis(1H,1H-perfluoropropyl)-naphthalene[1,8:4,5]bis(dicarboximide)

0.655 g (2.28 mmol) of N,N'-dibromoisocyanuric acid were added to a solution of 1.10 g of (2.07 mmol) N,N'-bis(1H,1H-perfluoropropyl)-naphthalene-[1,8:4,5]bis-(dicarboximide) in 160 mL of 95 to 97% strength sulfuric acid at room temperature. The solution was stirred for 40 hours at room temperature. Subsequently, the reaction mixture was poured on 1 L of icewater. The precipitate was filtered off and purified by column chromatography (dichloromethane/pentane 1:1) several times. 0.205 g (14% yield) of a light yellow solid were obtained.

$^1$H-NMR (400 MHz, CDCl$_3$): δ=9.08 (s, 2H), 4.99 (q, 4H, J=14.7 Hz) ppm.

Example 4

2,6-Dibromo-N,N'-bis(1H,1H-perfluoropentyl)-naphthalene[1,8:4,5]bis(dicarboximide) (compound of formula I, where R$^1$ and R$^2$ are 2,2,3,3,4,4,5,5,5-nonafluoropentyl)

4.1 N,N'-Bis(1H,1H-perfluoropentyl)-naphthalene[1,8:4,5]bis(dicarboximide)

The title compound was prepared as described in J. H. Oh et al., Adv. Funct. Mater. 2010, 20, 2148-2156.

$^1$H-NMR (400 MHz, CDCl$_3$): δ=8.87 (s, 4H), 5.04 (t, JHF=15.2 Hz, 4H) ppm.

4.2 2,6-Dibromo-N,N'-bis(1H,1H-perfluoropentyl)-naphthalene[1,8:4,5]bis(dicarboximide)

0.560 g (1.76 mmol) of N,N'-dibromoisocyanuric acid were added to a solution of 1.00 g (1.34 mmol) of N,N'-bis(1H,1H-perfluoropropyl)-naphthalene-[1,8:4,5]bis-(dicarboximide) in 140 mL of 95 to 97% strength sulfuric acid at room temperature. The solution was stirred for 40 hours at room temperature. Subsequently, the reaction mixture was poured on 1 l icewater. The precipitate was filtered off and purified by column chromatography (dichloromethane/pentane 1:1) several times, and then by recrystallization in ethyl acetate. 0.344 g (29% yield) of a light yellow solid were obtained.

1H-NMR (400 MHz, CDCl$_3$): δ=9.08 (s, 2H), 5.05 (q, 4H, J=15.6 Hz) ppm.

Example 5

General Procedure for the Fabrication of Vapor-Deposited OFETs in the Bottom-Gate Top-Contact Configuration Highly doped p-type silicon (100) wafers (0.01-0.02 Ω·cm) were used as substrates A. Highly doped p-type silicon (100) wafers (0.005-0.02 Ω·cm) with a 100 nm thick thermally grown SiO$_2$ layer (capacitance 34 nF/cm2) were used as substrates B.

Onto substrates A, a 30 nm thick layer of aluminum is deposited by thermal evaporation in a Leybold UNIVEX 300 vacuum evaporator from a tungsten wire, at a pressure of 2×10$^{-6}$ mbar and with an evaporation rate of 1 nm/s. The surface of the aluminum layer is oxidized by a brief exposure to an oxygen plasma in an Oxford reactive ion etcher (RIE, oxygen flow rate: 30 sccm, pressure: 10 mTorr, plasma pow-power: 200 W, plasma duration 30 sec) and the substrate is then immersed into a 2-propanol solution of a phosphonic acid (1 mMol solution of C$_{14}$H$_{29}$PO(OH)$_2$ [TDPA] or 1 mMol solution of C$_7$F$_{15}$C$_{11}$H$_{22}$PO(OH)$_2$ [FODPA]) and left in the solution for 1 hour, which results in the formation of a self-assembled monolayer (SAM) of phosphonic acid molecules on the aluminum oxide surface. The substrate is taken out of the solution and rinsed with pure 2-propanol, dried in a stream of nitrogen and left for 10 min on a hotplate at a temperature of 100° C. The total capacitance of the AlO$_x$/SAM gate dielectric on substrate A is 810 nF/cm$^2$ in case of C$_{14}$H$_{29}$PO(OH)$_2$ and 710 nF/cm$^2$ in case of C$_7$F$_{15}$C$_{11}$H$_{22}$PO(OH)$_2$.

On substrates B, an about 8 nm thick layer of Al$_2$O$_3$ is deposited by atomic layer deposition in a Cambridge NanoTech Savannah (80 cycles at a substrate temperature of 250° C.). The surface of the aluminum oxide layer is activated by a brief exposure to an oxygen plasma in an Oxford reactive ion etcher (RIE, oxygen flow rate: 30 sccm, pressure: 10 mTorr, plasma power: 200 W, plasma duration 30 sec) and the substrate is then immersed into a 2-propanol solution of a phosphonic acid (1 mMol solution of C$_{14}$H$_{29}$PO(OH)$_2$ [TDPA] or 1 mMol solution of C$_7$F$_{15}$C$_{11}$H$_{22}$PO(OH)$_2$ [FODPA]) and left in the solution for 1 hour, which results in the formation of a self-assembled monolayer (SAM) of phosphonic acid molecules on the aluminum oxide surface. The substrate is taken out of the solution and rinsed with pure 2-propanol, dried in a stream of nitrogen and left for 10 min on a hotplate at a temperature of 100° C. The total capacitance of the SiO$_2$/AlO$_x$/SAM gate dielectric on substrate B is 32 nF/cm$^2$ (independent on the choice of the phosphonic acid).

The contact angle of water on the TDPA-treated substrates is 108°, and on the FODPA-treated substrates 118°.

A 30 nm thick film of the organic semiconductor is deposited by thermal sublimation in a Leybold UN IVEX 300 vacuum evaporator from a molybdenum boat, at a pressure of 2×10$^{-6}$ mbar and with an evaporation rate of 0.3 nm/s.

For the source and drain contacts 30 nm of gold is evaporated through a shadow mask in a Leybold UNIVEX 300 vacuum evaporator from tungsten boat, at a pressure of 2×10$^{-6}$ mbar and with an evaporation rate of 0.3 nm/s. The transistors have a channel length (L) ranging from 10 to 100 µm and a channel width (W) ranging from 50 to 1000 µm.

To be able to contact the back side of the silicon wafer, the wafer (which also serves as the gate electrode of the transistors) is scratched on the back side and coated with silver ink.

The electrical characteristics of the transistors are measured on a Micromanipulator 6200 probe station using an Agilent 4156C semiconductor parameter analyzer. All measurements are performed in air at room temperature. The probe needles are brought into contact with the source and drain contacts of the transistors by putting them down carefully on top of the gold contacts. The gate electrode is contacted through the metal substrate holder onto which the wafer is placed during the measurements.

To obtain the transfer curve the drain-source voltage ($V_{DS}$) is held to 3 V (in case of substrate A) or 40 V (in case of substrate B). The gate-source voltage $V_{GS}$ is swept at medium speed from 0 to 3 V in steps of 0.03 V (substrate A) or from 0 to 40 V in steps of 0.4 V (substrate B) and back. The charge-carrier mobility is extracted in the saturation regime from the slope of $(I_D)^{1/2}$ versus $V_{GS}$.

To obtain the output characteristics the drain-source voltage ($V_{DS}$) is swept at medium speed from 0 to 3 V in steps of 0.03 V (substrate A) and from 0 to 40 V in steps of 0.4 V (substrate B), while the gate-source voltage $V_{GS}$ is held at up to 8 different voltages (e.g. 0, 0.5, 1, 1.5, 2, 2.5, 3 V in case of substrate A or 0, 10, 20, 30, 40 V in case of substrate B).

Table 1 gives the field-effect mobilities (µ) and on/off ratios ($I_{on}/I_{off}$) for semi-conductors with a thick (substrate B) gate dielectric with a certain SAM layer at a certain substrate temperature ($T_{sub}$) measured in ambient air.

TABLE 1

| Semi-conductor from example | Substrate | SAM | Substrate temperature $T_{sub}$ [° C.] | Field-effect mobility µ [cm$^2$/Vs] | On/Off ratio $I_{on}/I_{off}$ |
|---|---|---|---|---|---|
| 1* | B | C$_{14}$H$_{29}$PO(OH)$_2$ | 50 | 0.90 | 5 × 10$^6$ |
| 1* | B | F$_{15}$C$_7$H$_{22}$C$_{11}$PO(OH)$_2$ | 50 | 1.02 | 10$^7$ |
| 2 | B | C$_{14}$H$_{29}$PO(OH)$_2$ | 50 | 1 | 2 × 10$^8$ |
| 3 | B | C$_{14}$H$_{29}$PO(OH)$_2$ | 50 | 0.85 | 2 × 10$^8$ |
| 4 | B | F$_{15}$C$_7$H$_{22}$C$_{11}$PO(OH)$_2$ | 70 | 0.7 | 2 × 10$^7$ |

*comparison

Example 6

Procedure for a Solution-Processed OFET on a Standard Substrate in the Top-Gate Bottom-Contact Configuration A 0.5% solution of the semiconductor in ethyl acetate warmed to 50° C. was spincoated (Spin Coater: Primus STT15) on a standard PET substrate at 1000 rpm. The standard PET substrate consisted of a PET foil (Mitsubishi DN4600) with shadow-mask patterned, 50 nm thick gold Source and Drain contacts. After deposition of the semiconductor, Cytop CTL-809 (9%) was spincoated at 3500 rpm as a dielectric layer (thickness 660 nm, ∈$_r$=2,1). Immediately after spincoating, the substrate was placed on a hot-plate an annealed for 10 min at 100° C. Finally, 50 nm thick gate electrodes has been patterned by thermal evaporation of gold through a shadow-mask.

The electrical characteristics of the transistor was measured with an Agilent 4155C Semiconductor Parameter Analyzer. The transistor had a channel width (W) of 500 µm and a channel length (L) of 50 µm. All measurements were performed in air at room temperature.

To obtain the transfer curve the drain-source voltage ($U_{DS}$) is held to 40 V. The gate-source voltage $U_{GS}$ is swept at medium speed from −20 to 60 V in steps of 2 V and back. The charge-carrier mobility is extracted in the saturation regime from the slope m of $(I_D)^{1/2}$ versus $V_{GS}$ using the following equations:

$$\mu = \frac{m^2 * 2L}{C_G * W} \quad C_G = \varepsilon_0 * \varepsilon_r \frac{1}{d}$$

where ∈$_0$ is the vacuum permittivity of 8.85×10$^{-12}$ As/Vm.

To obtain the output characteristics the drain-source voltage ($V_{DS}$) is swept at medium speed from 0 to 60 V in steps of 2 V, while the gate-source voltage $V_{GS}$ is held at up to 5 different voltages (e.g. 0, 15, 30, 45, 60 V).

Table 2 gives the threshold voltage $U_{th}$, the field-effect mobilities (µ) and on/off ratios ($I_{on}/I_{off}$) for a solution-processed OFET on a silicon wafer in the top-gate bottom-contact configuration measured in ambient air.

TABLE 2

| Semiconductor from example | Threshold voltage $U_{th}$ [V] | Field-effect mobility µ [cm$^2$/Vs] | On/Off ratio $I_{on}/I_{off}$ |
|---|---|---|---|
| 1* | 16.9 | 0.061 | 1.7 × 10$^2$ |
| 4 | 11.0 | 0.17 | 2.5 × 10$^2$ |

*comparison

Example 7

Procedure for a Solution-Processed OFET on a Silicon Wafer in the Bottom-Gate Bottom-Contact Configuration A 0.5% solution of the semiconductor in ethyl acetate warmed to 50° C. was spincoated (Spin Coater: Primus STT15) on an untreated standard silicon substrate at 1000 rpm. The standard silicon substrate consisted of a silicon wafer with a 230 nm thick silicon dioxide layer (∈$_r$=3.9) and lithographically patterned S/D contacts consisting of 30 nm thick gold and ITO adhesive.

The electrical characteristics of the transistors were measured with an Agilent 4155C Semiconductor Parameter Analyzer. The transistors had a channel width (W) of 10000 µm and a channel length (L) of 10 µm. All measurements were performed in air at room temperature.

To obtain the transfer curve the drain-source voltage ($U_{DS}$) is held to 40 V. The gate-source voltage $U_{GS}$ is swept at medium speed from −20 to 40 V in steps of 2 V and back. The charge-carrier mobility is extracted in the saturation regime from the slope of $(I_D)^{1/2}$ versus $V_{GS}$.

To obtain the output characteristics the drain-source voltage ($V_{DS}$) is swept at medium speed from 0 to 40 V in steps of 2 V, while the gate-source voltage $V_{GS}$ is held at up to 5 different voltages (e.g. 0, 10, 20, 30, 40 V).

Table 3 gives the field-effect mobilities (μ) and on/off ratios ($I_{on}/I_{off}$) for a solution-processed OFET on a silicon wafer in the bottom-gate bottom-contact configuration measured in ambient air.

TABLE 3

| Semiconductor from example | Threshold voltage $U_{th}$ [V] | Mobility μ [cm²/Vs] | On/Off ratio $I_{on}/I_{off}$ |
| --- | --- | --- | --- |
| 1* | 3.2 | 0.00024 | 5.3 × 10⁴ |
| 4 | 7.5 | 0.0011 | 1.4 × 10⁵ |

*comparison

The invention claimed is:

1. A compound of formula I

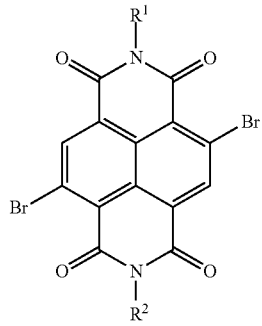

where
R¹ and R², independently of each other, are 2,2,2-trifluoroethyl or 2,2,3,3,3-pentafluoropropyl.

2. The compound according to claim 1, wherein R¹ and R² are the same.

3. The compound according to claim 1, is
2,6-dibromo-N,N-bis(2,2,2-trifluoroethyl)-naphthalene [1,8:4,5]bis(dicarboximide); or
2,6-dibromo-N,N-bis(1H,1H-pentafluoropropyl)-naphthalene-[1,8:4,5]bis(dicarboximide).

4. A semiconductor, comprising the compound according to claim 1.

5. A thin film semiconductor, comprising the compound according to claim 1.

6. An organic field effect transistor, comprising
a substrate comprising at least one gate structure,
a source electrode and a drain electrode, and
at least one compound according to claim 1 as a semiconductor material.

7. The organic field effect transistor according to claim 6, having a top-gate bottom-contact configuration.

8. The organic field effect transistor according to claim 6, having a bottom-gate bottom-contact configuration.

9. A substrate, comprising
a plurality of organic field-effect transistors,
wherein at least some of the field-effect transistors comprising at least one compound according to claim 1.

10. A semiconductor unit, comprising at least one substrate according to claim 9.

11. An organic solar cell, comprising at least one compound according to claim 1.

12. A semiconductor, comprising the compound according to claim 3.

13. A thin film semiconductor, comprising the compound according to claim 3.

14. An organic field effect transistor, comprising
a substrate comprising at least one gate structure,
a source electrode and a drain electrode, and
at least one compound according to claim 3 as a semiconductor material.

15. A substrate, comprising
a plurality of organic field-effect transistors,
wherein at least some of the field-effect transistors comprising at least one compound according to claim 3.

16. An organic solar cell, comprising at least one compound according to claim 3.

* * * * *

UNITED STATES PATENT AND TRADEMARK OFFICE
CERTIFICATE OF CORRECTION

PATENT NO. : 10,186,664 B2
APPLICATION NO. : 15/318566
DATED : January 22, 2019
INVENTOR(S) : Thomas Gessner et al.

Page 1 of 1

It is certified that error appears in the above-identified patent and that said Letters Patent is hereby corrected as shown below:

In the Specification

Column 3, Line 6, "devices" should read --devices.--;
　　　Line 59, "p" should read --µ"--.

Column 8, Line 33, "spincoating." should read --spin-coating--.

Column 9, Line 9, "US US" should read --US--;
　　　Line 18, "($C_1$)" should read --(C1)--.

Column 12, Line 21, "bathocuproin" should read --bathocuproine--.

Column 20, Line 61, "on" should read --one--.

Signed and Sealed this
Nineteenth Day of November, 2019

Andrei Iancu
*Director of the United States Patent and Trademark Office*